(12) United States Patent
Crew et al.

(10) Patent No.: US 7,498,354 B2
(45) Date of Patent: Mar. 3, 2009

(54) PYRROLO[2,3-D]IMIDAZOLES FOR THE TREATMENT OF HYPERPROLIFERATIVE DISORDERS

(75) Inventors: Andrew Philip Crew, Farmingdale, NY (US); Bijoy Panicker, Farmingdale, NY (US); Han-Qing Dong, Farmingdale, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 443 days.

(21) Appl. No.: 11/397,031

(22) Filed: Mar. 30, 2006

(65) Prior Publication Data

US 2006/0223799 A1    Oct. 5, 2006

(51) Int. Cl.
*A61K 31/4162* (2006.01)
*C07D 235/00* (2006.01)

(52) U.S. Cl. .................. 514/396; 548/300.1; 548/301.7; 548/302.7; 548/303.1; 546/268.1; 546/268.4; 546/273.1; 544/106; 544/111; 544/132; 544/139; 514/385; 514/393

(58) Field of Classification Search .............. 548/300.1, 548/301.7, 302.7, 303.1; 546/268.1, 268.4, 546/273.1; 544/106, 111, 132, 139; 514/385, 514/393, 396

See application file for complete search history.

*Primary Examiner*—Golam M Shameem

(57) ABSTRACT or a pharmaceutically acceptable salt or N-oxide thereof, are useful in the treatment of tumors and cancers.

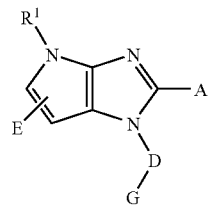

13 Claims, No Drawings

PYRROLO[2,3-D]IMIDAZOLES FOR THE TREATMENT OF HYPERPROLIFERATIVE DISORDERS

BACKGROUND OF THE INVENTION

The present invention is directed to pyrrolo[2,3-d]imidazole compounds. In particular, the present invention is directed to pyrrolo[2,3-d]imidazole compounds that are inhibitors of the c-Kit proto-oncogene (also known as KIT, CD-117, stem cell factor receptor, mast cell growth factor receptor).

The c-Kit proto-oncogene is believed to be important in embryogenesis, melanogenesis, hematopoiesis, and the pathogenesis of mastocytosis, gastrointestinal tumors, and other solid tumors, as well as certain leukemias, including AML. Accordingly, it would be desirable to develop novel compounds that are inhibitors of the c-Kit receptor.

Many of the current treatment regimes for hyperproliferative disorders (cancer) utilize compounds that inhibit DNA synthesis. Such compounds' mechanism of operation is to be toxic to cells, particularly to rapidly dividing tumor cells. Thus, their broad toxicity can be a problem to the subject patient. However, other approaches to anti-cancer agents that act other than by the inhibition of DNA synthesis have been explored to try to enhance the selectivity of the anti-cancer action and thereby reduce adverse side-effects.

It is known that a cell may become cancerous by virtue of the transformation of a portion of its DNA into an oncogene (i.e. a gene which, on activation, leads to the formation of malignant tumor cells). Many oncogenes encode proteins that are aberrant protein-tyrosine kinases capable of causing cell transformation. By a different route, the overexpression of a normal proto-oncogenic tyrosine kinase can also result in proliferative disorders, sometimes resulting in a malignant phenotype. Alternatively, co-expression of a receptor tyrosine kinase and its cognate ligand within the same cell type may also lead to malignant transformation.

Receptor tyrosine kinases are large enzymes which span the cell membrane and possess i) an extracellular binding domain for growth factors such as KIT ligand (also known as stem cell factor (SCF), Steel factor (SLF) or mast cell growth factor (MGF)), ii) a transmembrane domain, and iii) an intracellular portion which functions as a kinase to phosphorylate specific tyrosine residues in proteins. Binding of KIT ligand to KIT tyrosine kinase results in receptor homodimerization, the activation of KIT tyrosine kinase activity, and the subsequent phosphorylation of a variety of protein substrates, many of which are effectors of intracellular signal transduction, These events can lead to enhanced cell proliferation or promote enhanced cell survival. With some receptor kinases, receptor heterodimerization can also occur.

It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. KIT kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma.

Several mechanisms of KIT activation in tumor cells have been reported, including activating mutations, autocrine and paracrine activation of the receptor kinase by its ligand, loss of protein-tyrosine phosphatase activity, and cross activation by other kinases. The transforming mechanisms initiated by the activating mutations are thought to include dimer formation and increased intrinsic activity of the kinase domain, both of which result in constitutive ligand-independent kinase activation, and possibly altered substrate specificity. More than thirty activating mutations of the Kit protein have been associated with highly malignant tumors in humans.

Accordingly, it has been recognized that inhibitors of receptor tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. Gleevec™, in addition to inhibiting BCR-ABL kinase, also inhibits the KIT kinase and PDGF receptor kinase, although it is not effective against all mutant isoforms of the KIT kinase. Kit ligand-stimulated growth of MO7e human leukemia cells is inhibited by Gleevec™, which also induces apoptosis under these conditions. By contrast, GM-CSF stimulated growth of MO7e human leukemia cells is not affected by Gleevec™. Further, in recent clinical studies using Gleevec™ to treat patients with GIST, a disease in which KIT kinase is involved in transformation of the cells, many of the patients showed marked improvement.

These studies demonstrate how KIT kinase inhibitors can treat tumors whose growth is dependent on KIT kinase activity. Other kinase inhibitors show even greater kinase selectivity. For example, the 4-anilinoquinazoline compound Tarceva™ inhibits only EGF receptor kinase with high potency, although it can inhibit the signal transduction of other receptor kinases, probably by virtue of the fact that these receptors heterodimerize with EGF receptor.

Although anti-cancer compounds such as those described above make a significant contribution to the art, there is a continuing need for improved anti-cancer pharmaceuticals, and it would be desirable to develop new compounds with better selectivity or potency, or with reduced toxicity or side effects.

SUMMARY OF THE INVENTION

Compounds represented by Formula (I):

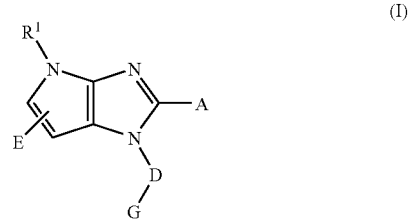

or a pharmaceutically acceptable salt or N-oxide thereof, are useful in the treatment of tumors and cancers.

DETAILED DESCRIPTION OF THE INVENTION

The present invention is directed to a compound represented by Formula (I):

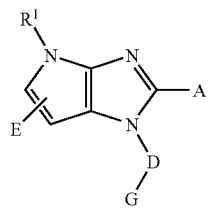

or a pharmaceutically acceptable salt or N-oxide thereof, wherein
A is $C_{0-6}$alkyl or —$NR^1R^{11}$;
E is —$CO_2R^2$, —$CONR^{12}R^{21}$, —$C(R^aR^b)OR^{212}$, or —$C(R^aR^b)NR^{12}R^2$;
D is aryl or hetaryl;
G is $C_{0-6}$alkyl, halogen, optionally substituted cyclyl, optionally substituted heterocyclyl, —$OR^{22}$, —$NR^{13}R^{22}$, —CN or —$CF_3$;
$R^1$, $R^{11}$, $R^{12}$, $R^{212}$, and $R^{13}$ each independently is $C_{0-6}$alkyl, —$COR^{14}$, —$CONR^{14}R^{15}$, or —$S(O)_nNR^{14}R^{15}$;
$R^{14}$ and $R^{15}$ each independently is $C_{0-6}$alkyl, —$CO(C_{0-6}$alkyl), —$CON(C_{0-6}$alkyl)($C_{0-6}$alkyl), or —$S(O)_mN(C_{0-6}$alkyl)($C_{0-6}$alkyl);
$R^2$ and $R^{22}$ each independently is $C_{1-8}$alkyl optionally substituted with a heterocyclyl; —$C_{0-8}$alkyl-$C_{3-8}$cycloalkyl, —$C_{2-8}$alkyl-O—$C_{0-8}$alkyl, —$C_{2-8}$alkyl-N($C_{0-8}$alkyl)($C_{0-8}$alkyl), —$C_{2-8}$alkyl-$S(O)_{0-2}$—$C_{0-8}$alkyl; or heterocyclyl optionally substituted with $C_{0-8}$alkyl, cyclyl or substituted cyclyl substituent;
$R^{21}$ is $C_{0-8}$alkyl optionally substituted with a heterocyclyl; $R^{21}$ is —$C_{0-8}$alkyl-$C_{3-8}$cycloalkyl, —$C_{2-8}$alkyl-O—$C_{0-8}$alkyl, —$C_{2-8}$alkyl-N($C_{0-8}$alkyl)($C_{0-8}$alkyl), or —$C_{2-8}$alkyl-$S(O)_{0-2}$—$C_{0-8}$alkyl; or $R^{21}$ is heterocyclyl optionally substituted with $C_{0-8}$alkyl, cyclyl or substituted cyclyl substituent;
$R^a$ and $R^b$ are each independently $C_{0-8}$alkyl or $C_{3-8}$cycloalkyl;
or $R^a$ and $R^b$ taken together with the C to which they are attached form a saturated or partially unsaturated 3-10 membered ring optionally containing 0-4 N, O, S, SO, or $SO_2$ at the ring nodes, provided that no N, O or S atoms are placed adjacent to each other at ring nodes; and
n and m each independently is 0, 1, or 2.

In one aspect, the present invention is directed to a compound represented by Formula (I), or a pharmaceutically acceptable salt or N-oxide thereof, wherein A is $C_{0-6}$alkyl; and the other variables are as described above for Formula (I).

In an embodiment of this one aspect, the present invention is directed to a compound represented by Formula (I), or a pharmaceutically acceptable salt or N-oxide thereof, wherein A is $C_{0-6}$alkyl, E is —$CO_2R^2$, and the other variables are as described above for Formula (I).

In another embodiment of this one aspect, the present invention is directed to a compound represented by Formula (I), or a pharmaceutically acceptable salt or N-oxide thereof, wherein A is $C_{0-6}$alkyl, E is —$CONR^{12}R^{21}$, and the other variables are as described above for Formula (I).

In still another embodiment of this one aspect, the present invention is directed to a compound represented by Formula (I), or a pharmaceutically acceptable salt or N-oxide thereof, wherein A is $C_{0-6}$alkyl, E is —$C(R^aR^b)OR^{212}$, and the other variables are as described above for Formula (I).

In yet another embodiment of this one aspect, the present invention is directed to a compound represented by Formula (I), or a pharmaceutically acceptable salt or N-oxide thereof, wherein A is $C_{0-6}$alkyl, E is —$C(R^aR^b)NR^{12}R^2$, and the other variables are as described above for Formula (I).

In a second aspect, the present invention is directed to a compound represented by Formula (I), or a pharmaceutically acceptable salt or N-oxide thereof, wherein A is —$NR^1R^{11}$; and the other variables are as described above for Formula (I).

In a third aspect, the present invention is directed to a compound represented by Formula (I), or a pharmaceutically acceptable salt or N-oxide thereof, wherein D is aryl.

In an embodiment of this third aspect, the present invention is directed to a compound represented by Formula (I), or a pharmaceutically acceptable salt or N-oxide thereof, wherein D is aryl, G is $C_{0-6}$alkyl, and the other variables are as described above for Formula (I).

In another embodiment of this third aspect, the present invention is directed to a compound represented by Formula (I), or a pharmaceutically acceptable salt or N-oxide thereof, wherein D is aryl, G is halogen, and the other variables are as described above for Formula (I).

In yet another embodiment of this third aspect, the present invention is directed to a compound represented by Formula (I), or a pharmaceutically acceptable salt or N-oxide thereof, wherein D is aryl, G is optionally substituted heterocyclyl, and the other variables are as described above for Formula (I).

The compounds of the present invention include

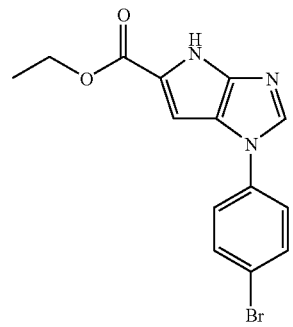

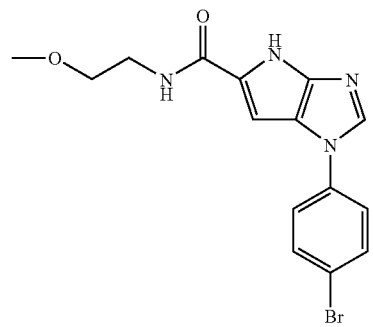

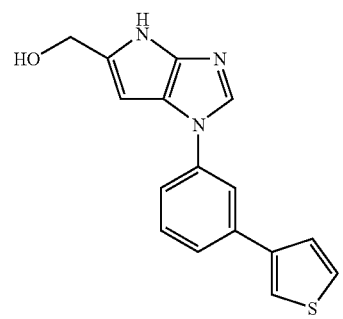

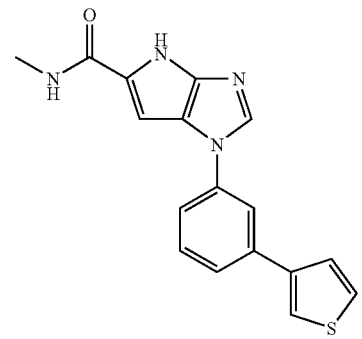

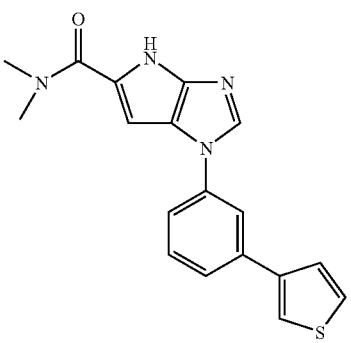

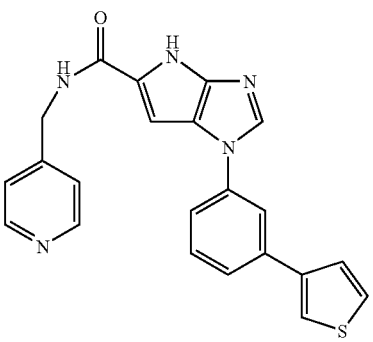

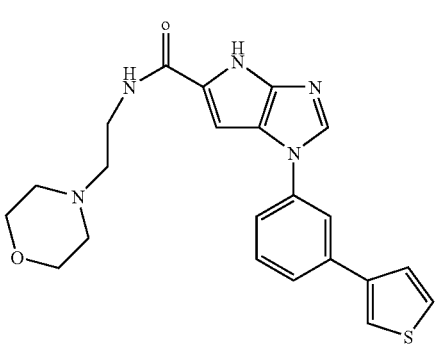

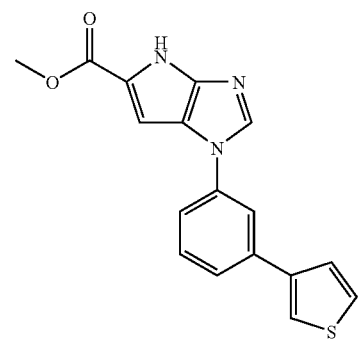

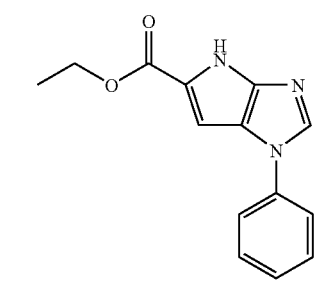

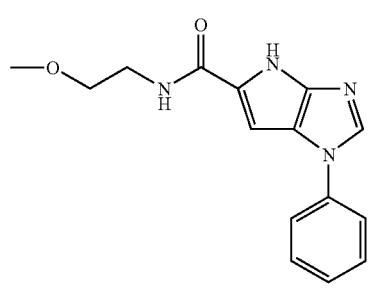

or a pharmaceutically acceptable salt or N-oxide thereof.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, "$C_{0-6}$alkyl" is used to mean an alkyl having 0-6 carbons—that is, 0, 1, 2, 3, 4, 5, or 6 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl", "carbocyclic ring", "cyclic", or "cyclyl" mean 3-10 membered mono or polycyclic aromatic, partially aromatic or non-aromatic ring carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$ cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms. The term "carbamoyl" unless specifically described otherwise means —C(O)—NH— or —NH—C(O)—.

The term "aryl" is well known to chemists. The preferred aryl groups are phenyl and naphthyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocycle", "heterocyclic", and "heterocyclyl" are equivalent, and is defined as for cyclic but also contains one or more atoms chosen independently from N, O, and S (and the N and S oxides), provided such derivatives exhibit appropriate and stable valencies and excludes moieties containing O—O, $S(O)_n$—$S(O)_n$, $S(O)_n$—O bonds where n=0-2. The terms include 4-8-membered saturated rings containing one or two heteroatoms chosen from oxygen, sulfur, and nitrogen. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, azepane, azocane, [1,3]dioxane, oxazolidine, piperazine, homopiperazine, morpholine, thiomorpholine, and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems, including het-het fused systems, and can include a carbocyclic ring that is partially or fully unsaturated, such as a benzene ring, to form benzofused heterocycles. For example, 3,4,-dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier. Preferably, the composition is comprised of a pharmaceutically acceptable carrier and a non-toxic therapeutically effective amount of a compound of Formula I as described above (or a pharmaceutically acceptable salt or N-oxide thereof).

Moreover, within this preferred embodiment, the invention encompasses a pharmaceutical composition for the treatment of disease by the inhibition of the c-Kit kinase, which may be a wild-type or mutant form of the protein, comprising a pharmaceutically acceptable carrier and a non-toxic therapeutically effective amount of compound of Formula I as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrochloric, maleic, phosphoric, sulfuric, methanesulfonic, and tartaric acids.

The pharmaceutical compositions of the present invention comprise a compound represented by formula I (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula I. The compounds of Formula I, or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula I or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts or N-oxides thereof, may also be prepared in powder or liquid concentrate form.

Generally, dosage levels on the order of from about 0.01 mg/kg to about 750 mg/kg of body weight per day are useful in the treatment of the above-indicated conditions, or alternatively about 0.5 mg to about 75 g per patient per day. For example, breast cancer, head and neck cancers, and gastrointestinal cancer such as colon, rectal or stomach cancer may be effectively treated by the administration of from about 0.01 to 500 mg of the compound per kilogram of body weight per day, or alternatively about 0.5 mg to about 50 g per patient per day.

Similarly, leukemia, ovarian, bronchial, lung, and pancreatic cancer may be effectively treated by the administration of from about 0.01 to 500 mg of the compound per kilogram of body weight per day, or alternatively about 0.5 mg to about 50 g per patient per day.

Mastocytosis/mast cell leukemia, gastrointestinal stromal tumors (GIST), small cell lung carcinoma (SCLC), colon cancer, sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma may be effectively treated by the administration of from about 0.01 to 500 mg of the compound per kilogram of body weight per day, or alternatively about 0.5 mg to about 50 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other cancer therapeutic compounds. For example, cytotoxic agents and angiogenesis inhibiting agents can be advantageous co-agents with the compounds of the present invention. Accordingly, the present invention includes compositions comprising the compounds represented by Formula I, or a pharmaceutically acceptable salt or N-oxide thereof, and a cytotoxic agent or an angiogenesis-inhibiting agent. The amounts of each can be therapeutically effective alone—in which case the additive effects can overcome cancers resistant to treatment by monotherapy. The amounts of any can also be subtherapeutic—to minimize adverse effects, particularly in sensitive patients.

It is understood that the treatment of cancer depends on the type of cancer. For example, lung cancer is treated differently as a first line therapy than are colon cancer or breast cancer treated. Even within lung cancer, for example, first line therapy is different from second line therapy, which in turn is different from third line therapy. Newly diagnosed patients might be treated with cisplatinum containing regimens. Were that to fail, they move onto a second line therapy such as a taxane. Finally, if that failed, they might get a tyrosine kinase EGFR inhibitor as a third line therapy. Further, The regulatory approval process differs from country to country. Accordingly, the accepted treatment regimens can differ from country to country. Nevertheless, the compounds of the present invention, or pharmaceutically acceptable salts or N-oxides thereof, can be beneficially co-administered in conjunction or combination with other such cancer therapeutic compounds. Such other compounds include, for example, a variety of cytotoxic agents (alkylators, DNA topoisomerase inhibitors, antimetabolites, tubulin binders); inhibitors of angiogenesis; and different other forms of therapies including kinase inhibitors such as Tarceva, monoclonal antibodies, and cancer vaccines. Other such compounds that can be beneficially co-administered with the compounds of the present invention include doxorubicin, vincristine, cisplatin, carboplatin, gemcitabine, and the taxanes. Thus, the compositions of the present invention include a compound according to Formula I, or a pharmaceutically acceptable salt or N-oxide thereof, and an anti-neoplastic, anti-tumor, anti-angiogenic, or chemotherapeutic agent.

The compounds of the present invention, or pharmaceutically acceptable salts or N-oxides thereof, can also be effectively administered in conjunction with other therapeutic compounds, aside from cancer therapy. For example, therapeutic agents effective to ameliorate adverse side-effects can be advantageous co-agents with the compounds of the present invention.

I. Assay for Inhibition of c-Kit in Intact Cells

The ability of compounds to inhibit the tyrosine kinase activity of c-Kit was determined in a cell-based ELISA assay using the H526 cell line (ATCC # CRL-5811), which was originally derived from a human small cell lung cancer. The assay determines the ability of compounds to block ligand-stimulated tyrosine phosphorylation of the wild-type c-Kit receptor protein that is endogenously expressed in H526 cells. Cells are pre-incubated with compounds at various concentrations prior to addition of stem cell factor (SCF), the ligand for the c-Kit receptor tyrosine kinase. Cell lysates are then prepared and the c-Kit protein is captured onto a c-Kit antibody-coated 96-well ELISA plate. The phosphotyrosine content of the receptor protein is then monitored by quantitation of the degree of binding of an antibody that recognizes only the phosphorylated tyrosine residues within the captured protein. The antibody used has a reporter enzyme (e.g. horseradish peroxidase, HRP) covalently attached, such that binding of antibody to phosphorylated c-Kit can be determined quantitatively by incubation with an appropriate HRP substrate.

The stock reagents used are as follows:

Cell Lysis Buffer:
  50 mM Tris-HCl, pH 7.4
  150 mM NaCl
  10% Glycerol
  1% Triton X-100
  0.5 mM EDTA
  1 μg/mL leupeptin
  1 μg/mL aprotinin 1 mM Sodium orthovanadate Anti c-Kit antibody:

0.5 µg/mL anti c-Kit Ab-3 (Lab Vision, catalog #MS289P1) in 50 mM Sodium bicarbonate, pH 9.

ELISA Assay Plates:

ELISA assay plates are prepared by addition of 100 µL of anti c-Kit antibody to each well of a 96-well Microlite-2 plate (Dynex, catalog # 7417), followed by incubation at 37° C. for 2 h. The wells are then washed twice with 300 µL wash buffer.

Plate Wash Buffer:

PBS containing 0.5% Tween-20 (PBST)

Cell Assay Medium:

RPMI with 0.1% BSA pY20-HRP:

25 ng/mL pY20-HRP (Calbiochem, catalog # 525320) in PBS, containing 0.5% Tween-20, 5% BSA, 1 mM Sodium orthovanadate HRP Substrate:

Chemoluminescent detection reagent (Pierce, catalog # 37075)

Assay Protocol:

Cultures of H526 cells, growing in RPMI with 10% fetal calf serum, were collected by centrifugation, washed twice with PBS, and suspended in cell assay medium. Cells were then distributed into a V-bottom 96-well plate at $7.5 \times 10^4$ cells per well in 100 µL cell assay medium.

Compound dilutions were prepared from 10 mM DMSO stocks by dilution in cell assay medium, the final concentration of DMSO in the assay being 0.1%. To compound incubation wells, 50 µL of the test compound was added (compounds are assayed at concentrations between 0.1 nM and 100 µM); to positive and negative control wells, 50 µL cell assay medium containing 0.1% DMSO was added. The cells were then incubated with compound at 37° C. for 3 h. SCF (R&D Systems, catalog #255-SC-010) was then added in order to stimulate the Kit receptor and induce its tyrosine phosphorylation. Then, 10 µL of a 1.6 µg/mL solution of SCF in cell assay medium was added to all wells apart from the negative control wells, and the cells were incubated for an additional 15 min at 37° C. Following the addition of ice-cold PBS, the plate was centrifuged at 1000 rpm for 5 min, the medium removed by aspiration, and the cell pellet lysed by the addition of 120 µL ice-cold cell lysis buffer per well. The plate was kept on ice for 20 min and 100 µL of the cell lysates from each well were then transferred to the wells of an ELISA assay plate and incubated at 4° C. for 16 h.

Following incubation of the cell lysates in the ELISA plate, the wells were washed 4 times with 300 µL wash buffer, then 100 µL of the phosphotyrosine detection antibody pY20-HRP was added to each well and the plate incubated at rt for 2 h. The wells were then washed 4 times with 300 µL wash buffer. Then, 50 µL of the chemiluminescent HRP substrate was added to each well for luminometric quantitation of the amount of antiphosphotyrosine-HRP conjugate bound to the plate.

Comparison of the assay signals obtained in the presence of compound with those of the positive and negative controls (cells incubated in the presence or absence of SCF, with no compound added), allows the degree of inhibition of c-Kit receptor tyrosine phosphorylation to be determined over a range of compound concentrations. These inhibition values were fitted to a sigmoidal dose-response inhibition curve to determine the $IC_{50}$ values (i.e. the concentration of compound that inhibits SCF-induced tyrosine phosphorylation of the c-Kit protein by 50%).

II. Activated c-Kit Kinase Bench Assay cDNA encoding the c-Kit tyrosine kinase domain was isolated from K562 cells and cloned into a baculovirus expression vector for protein expression in insect cells as a fusion protein with GST (Glutathione S-Transferase). Following purification, the enzyme was incubated with ATP to generate a tyrosine phosphorylated, activated form of the enzyme, which was used in kinase assays to determine the ability of compounds to inhibit phosphorylation of an exogenous substrate by the c-Kit tyrosine kinase domain.

Phosphorylation of c-Kit protein

The reagents used were as follows:

Column Buffer:

50 mM HEPES pH 7.4

125 mM NaCl

10% Glycerol 1 mg/mL BSA 2 mM DTT

200 µM $NaVO_3$

Phosphorylation Buffer:

50 mM HEPES pH 7.4

125 mM NaCl 24 mM $MgCl_2$ 1 mM $MnCl_2$

1% Glycerol

200 µM $NaVO_3$ 2 mM DTT 2 mM ATP

75 µL purified GST-Kit tyrosine kinase protein (approximately 150 µg) is incubated with 225 µL phosphorylation buffer for 1 h at 30° C. In a cold room, a desalting column (e.g. Pharmacia PD-10 column) is equilibrated using 25 mL of column buffer. Phosphorylated protein is applied to the column followed by sufficient column buffer to equal 2.5 mL total (in this case 2.2 mL). The phosphorylated Kit protein is then eluted with 3.5 mL column buffer, and collected into a tube containing 3.5 mL glycerol (final concentration of 50% glycerol). After mixing, aliquots are stored at −20° C. or −70° C.

Kinase activity is determined in an ELISA-based assay that measures the ability of c-Kit to phosphorylate an exogenous substrate (poly Glu:Tyr) on tyrosine residues in the presence of ATP. Substrate phosphorylation is monitored by quantitation of the degree of binding of an antibody that recognizes only the phosphorylated tyrosine residues within the substrate following incubation with c-Kit. The antibody used has a reporter enzyme (e.g. horseradish peroxidase, HRP) covalently attached, such that binding of antibody to the phosphorylated substrate can be determined quantitatively by incubation with an appropriate HRP substrate (e.g. ABTS).

The Stock Reagents Used are as Follows:

13.3 µg/mL PGT stock solution: Add 66.7 µL 10 mg/mL PGT to 50 mL PBS.

1× wash buffer: Dilute 20× wash buffer (KPL #50-63-00) to 1× with $H_2O$.

Assay Buffer:

50 mM Hepes, pH 7.4

125 mM NaCl 24 mM $MgCl_2$ 1 mM $MnCl_2$

1% Glycerol

200 µM Vanadate—add immediately prior to use 2 mM DTT—add immediately prior to use Assay buffer+ATP: Add 5.8 µL of 75 mM ATP to 12 mL of assay buffer.

Activated GST-c-kit(TK): Dilute 1:500 in assay buffer.

Block Buffer:

PBS containing 0.5% Tween-20, 3% BSA

200 µM Vanadate—add immediately prior to use pY20-HRP:

Add 6.2 µL of a 100 µg/mL stock of pY20-HRP to 10 mL of block buffer

ABTS substrate: KPL 3 50-66-06, use as provided

Assay Protocol

Each well of a 94-well immulon-4 microtitre plate is coated with 75 µL of 13.3 µg/mL PGT stock solution, incubated overnight at 37° C. and washed once with 250 µL 1× wash buffer.

To the negative control wells, 50 µL of assay buffer (without ATP) are added, all other wells contain 50 µL assay buffer+ATP. To positive and negative control wells, 10 µl 5% DMSO is added, other wells contain 10 µL of test compounds (at concentrations between 10 nM and 100 µM) dissolved in 5% DMSO.

30 µL of activated GST-c-Kit are added to initiate the assay, which is incubated at RT for 30 min, and then stopped by the addition of 50 µL/well of 0.5M EDTA. The plate is washed 3× with 1× wash buffer, and then 75 µL of a phospho-tyrosine-specific antibody-HRP conjugate (e.g. pY20-HRP, Calbiochem) in block buffer are added. The plate is incubated at RT for 2 h, and then washed 3× with 1× wash buffer. 100 µL of ABTS substrate are then added, the plate is incubated at rt for 30 min, and the reaction stopped by the addition of 100 µL of 1% SDS. The reaction is quantitated by measuring the OD at 405/490 nM on a microtitre plate reader.

Comparison of the assay signals obtained in the presence of compound with those of controls (in the presence and absence of ATP, with no compound added), allows the degree of inhibition of kinase activity to be determined over a range of compound concentrations. These inhibition values were fitted to a sigmoidal dose-response inhibition curve to determine the IC50 values (i.e. the concentration of compound that inhibits c-Kit protein tyrosine kinase activity by 50%).

The EXAMPLES of this invention either reduced the level of SCF-induced tyrosine phosphorylation of Kit in intact H526 cells as determined in assay I with IC50 values between 10 µM and 0.4 nM, or reduced the ability of Kit to phosphorylate poly(Glu:Tyr) in assay II by at least 50% at 10 µM compound concentrations.

EXPERIMENTAL

The EXAMPLES of the present invention were prepared according to the following procedures and by the methods illustrated in the following scheme. Appropriate solvents, temperatures, pressures and other reaction conditions may be readily selected by one of ordinary skill in the art. Similarly, suitable starting materials may be commercially obtained or readily prepared by one skilled in the art.

Alternate functionalities to those specifically shown may be included into the target molecules through appropriate choice of starting materials. Where the final functionality is not available directly through this process, or where such functionality may be compromised during the subsequent chemistry to build the final molecule, alternative functionalities may be used and subsequently transformed into the final desired functionality by methods, and at points in the sequence, readily determined by one skilled in the art.

For example, a non-exhaustive list of such transformations includes the conversions: OMe→OH (BBr$_3$), NH$_2$→Cl (NaNO$_2$, CuCl), Br→CN (Pd$_2$(dba)$_3$, Zn(CN)$_2$, DPPF), Me→CO$_2$H (KMnO$_4$), CO$_2$H→CO$_2$Me (MeOH, H$_2$SO$_4$), OH→OAlkyl (Alkyl halide, base), CO$_2$H→CONR'R" (EDC, HOAt, DIPEA, HNR'R"), Br→CO$_2$Me (Pd$_2$(dba)$_3$, DPPF, CO(g), MeOH), Br→CO$_2$H (tBuLi, CO$_2$), Ar—H→Ar—Br (NBS), CN→CO$_2$H (conc. H$_2$SO$_4$), Br→NR'R" (Pd$_2$(dba)$_3$, DPPF, HNR'R").

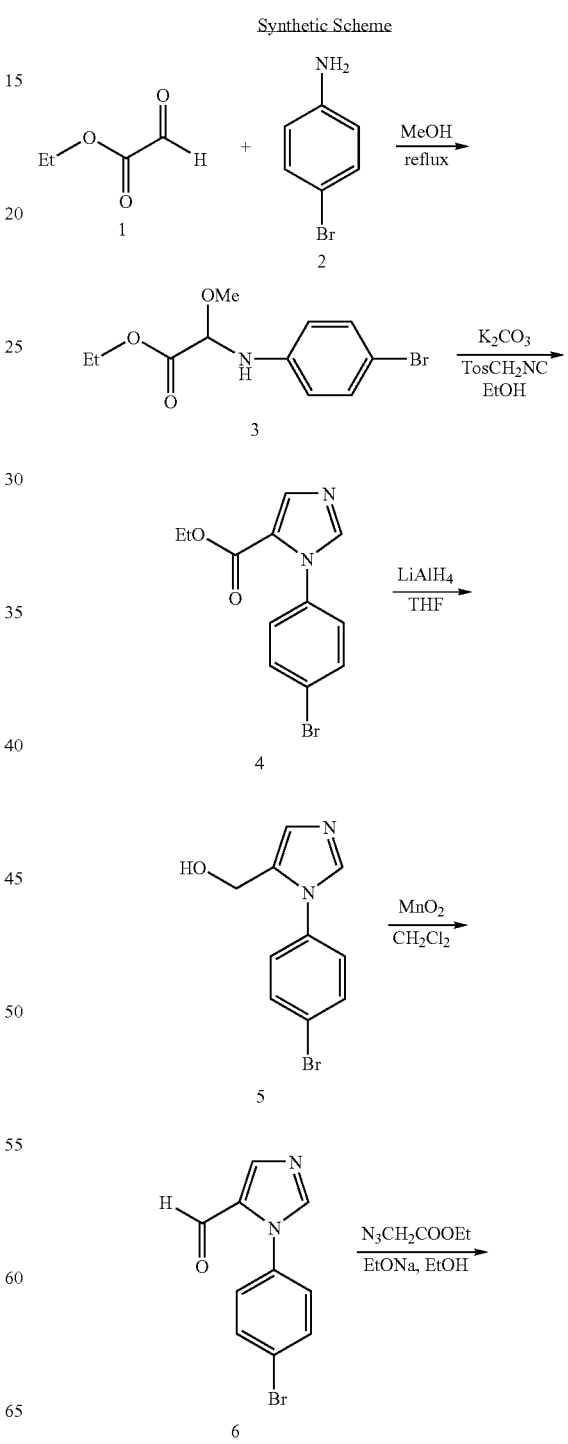

Synthetic Scheme

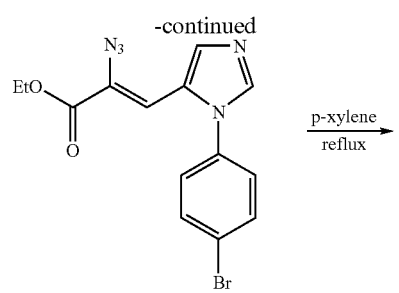

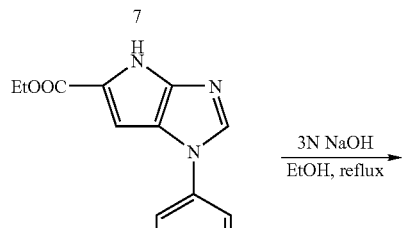

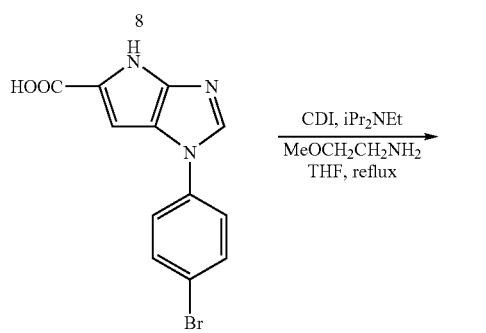

Synthetic Procedure

Ethyl 1-(4-bromophenyl)-1H-imidazole-5-carboxylate (4) was constructed through the condensation of tosylmethyl isocyanide and hemi-aminal 3, which in turn was produced by the addition of 4-bromoaniline (2) to ethyl glyoxalate (1). Ester 4 was reduced with LiAlH$_4$ at −40° C. and the resulting alcohol 5 oxidised with MnO$_2$ to furnish 1-(4-bromophenyl)-1H-imidazole-5-carbaldehyde (6), which was condensed with ethyl azidoacetate to give the α,β-unsaturated ester 7. The pyrrolo[2,3-d]imidazole core 8 was then formed by thermal cyclisation of 7 in refluxing in p-xylene. Hydrolysis of 8 provided 1-(4-bromophenyl)-1,4-dihydropyrrolo[2,3-d]imidazole-5-carboxylic acid (9) which could be coupled with various amines, for example, with 2-methoxyethylamine to give amide 10.

EXPERIMENTAL: CHEMISTRY AND EXAMPLES

Example 1

Ethyl 1-(4-bromophenyl)-1,4-dihydropyrrolo[2,3-d]imidazole-5-carboxylate

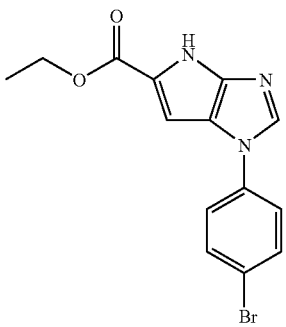

To a solution of 4-bromoaniline (8.6 g, 50 mmol) in MeOH (100 mL) was added ethyl glyoxalate (12 mL, 60 mmol, 50% in toluene) and the resulting mixture heated at reflux for 3.5 h. The mixture was then concentrated in vacuo and the resulting residue reconstituted in anhydrous ethanol (100 mL) and treated with tosylmethyl isocyanide (14.6 g, 75 mmol) and potassium carbonate (13.8 g, 100 mmol). The resulting mixture was heated at 65° C. for 4 h, then cooled to rt and poured to water (500 mL) and the resulting solid collected by filtration. The crude material thus isolated was crystallized from ethyl acetate/hexane to give pure 3-(4-bromophenyl)-3H-imidazole-4-carboxylic acid ethyl ester (4). MS (ES$^+$): m/z 295/297 (1/1) [MH$^+$]. $^1$H NMR (CDCl$_3$, 400 MHz): δ=1.27 (t, J=7.1 Hz, 3H), 4.22 (q, J=7.1 Hz, 2H), 7.22 (d, J=8.7 Hz, 2H), 7.61 (d, J=8.7 Hz, 2H), 7.65 (d, J=0.9 Hz, 1H) and 7.85 (d, J=0.9 Hz, 1H).

To a solution of 3-(4-bromophenyl)-3H-imidazole-4-carboxylic acid ethyl ester (4) (590 mg, 2.0 mmol) in dry THF was added lithium aluminium hydride (2.4 mL, 2.4 mmol, 1.0M in THF) dropwise at −40° C. under nitrogen, and the resulting mixture slowly warmed to −20° C. over 1 h. The reaction mixture was then quenched with saturated aqueous ammonium chloride solution (3 mL) at −20° C. and diluted with ethyl acetate (40 mL). The suspension was filtered and the filtrate was washed with brine (20 mL), dried over anhydrous sodium sulphate and concentrated in vacuo to afford [3-(4-bromophenyl)-3H-imidazol-4-yl]-methanol (5). MS (ES$^+$): m/z 253/255 (1/1) [MH$^+$]. $^1$H NMR (CDCl$_3$, 400 MHz): δ=2.25 (br s, 1H), 4.56 (s, 2H), 7.14 (s, 1H), 7.40 (d, J=8.8 Hz, 2H), 7.63 (s, 1H), 7.64 (d, J=8.8 Hz, 2H).

To a solution of [3-(4-bromophenyl)-3H-imidazol-4-yl]-methanol (5) (500 mg, 2.0 mmol) in dry methylene chloride (30 mL) was added MnO$_2$ (1.74 g, 20.0 mmol) and the resulting mixture stirred overnight at rt. The suspension was then filtered through Celite and the filtrate concentrated under reduced pressure to give 3-(4-bromophenyl)-3H-imidazole-4-carbaldehyde (6). MS (ES+): m/z 251/253 (1/1) [MH+]. 1H NMR (CDCl3, 400 MHz): δ=7.24 (d, J=8.7 Hz, 2H), 7.64 (d, J=8.7 Hz, 2H), 7.77 (s, 1H), 7.94 (s, 1H), 9.78 (s, 1H).

A commercially available 34% methylene chloride solution of ethyl azidoacetate (6.6 mL, 21.6 mmol) was concentrated in vacuo, the residue reconstituted in anhydrous ethanol (100 mL) and the resulting solution treated with 3-(4-bromophenyl)-3H-imidazole-4-carbaldehyde (6) (2.7 g, 10.8 mmol). The mixture was cooled to 0° C., treated dropwise with potassium ethoxide solution (5.1 mL, 13.0 mmol, 24% (w/w) EtOH solution) and the mixture stirred at 0° C. for 5 h. The resulting white solid was collected by filtration and dried in air to yield ethyl 2-azido-3-[3-(4-bromophenyl)-3H-imidazol-4-yl]acrylate (7). LC-MS (ES+): m/z 362/364 (1/1) [MH+]. 1H NMR (CDCl3, 400 MHz): δ=1.31 (t, J=7.1 Hz, 3H), 4.30 (q, J=7.1 Hz, 2H), 6.52 (d, J=0.7 Hz, 1H), 7.19 (d, J=8.7 Hz, 2H), 7.67 (s, 1H), 7.68 (d, J=8.7 Hz, 2H), 8.03 (d, J=0.7 Hz, 1H).

A suspension of ethyl 2-azido-3-[3-(4-bromophenyl)-3H-imidazol-4-yl]acrylate (7) (240 mg) in p-xylene (10 mL) was heated at reflux under nitrogen for 30 min. The mixture was then cooled to rt, and the resulting white solid was collected by filtration, washed with hexane, and dried in air to yield ethyl 1-(4-bromophenyl)-1,4-dihydropyrrolo[2,3-d]imidazole-5-carboxylate EXAMPLE 1. LC-MS (ES+): m/z 334/336 (1/1) [MH+]. 1H NMR (CDCl3, 400 MHz): δ=1.40 (t, J=7.1 Hz, 3H), 4.38 (q, J=7.1 Hz, 2H), 6.94 (d, J=1.6 Hz, 1H), 7.43 (d, J=8.8 Hz, 2H), 7.65 (d, J=8.8 Hz, 2H), 7.93 (s, 1H), 8.99 (br s, 1H).

Example 2

Ethyl 1-phenyl-1,4-dihydropyrrolo[2,3-d]imidazole-5-carboxylate

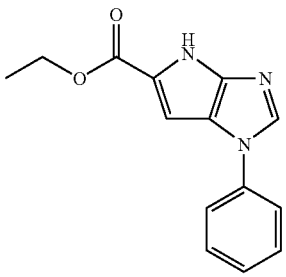

A suspension of ethyl 1-(4-bromophenyl)-1,4-dihydropyrrolo[2,3-d]imidazole-5-carboxylate (EXAMPLE 1) (50 mg) and 10% Pd—C (100 mg) in ethanol (10 mL) and ethyl acetate (10 mL), was hydrogenated at atmospheric pressure for 16 h. The catalyst was removed by filtration through Celite and the filtrate concentrated in vacuo to yield ethyl 1-phenyl-1,4-dihydropyrrolo[2,3-d]imidazole-5-carboxylate EXAMPLE 2. LC-MS (ES+): m/z 256 [MH+]. 1H NMR (DMSO-d6, 400 MHz): δ=1.46 (t, J=7.1 Hz, 3H), 4.42 (q, J=7.1 Hz, 2H), 7.22 (d, J=1.0 Hz, 1H), 7.48 (m, 1H), 7.69 (m, 2H), 7.94 (m, 2H), 8.73 (s, 1H), 12.28 (br s, 1H, NH).

Example 3

1-(4-Bromophenyl)-N-(2-methoxyethyl)-1,4-dihydropyrrolo[2,3-d]imidazole-5-carboxamide

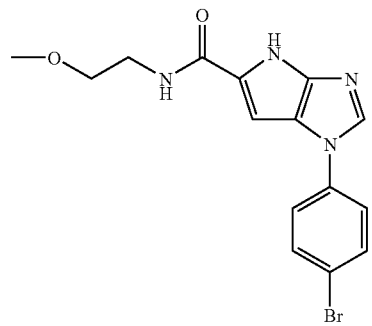

To a suspension of ethyl 1-(4-bromophenyl)-1,4-dihydropyrrolo[2,3-d]imidazole-5-carboxylate (EXAMPLE 1) (95 mg) in ethanol (3 mL) was added 1 mL of 3N NaOH and the mixture heated at reflux for 6 h, after which time mixture was cooled to rt and acidified with 3N HCl to pH=3. The resulting off-white solid was collected by filtration to yield 1-(4-bromophenyl)-1,4-dihydropyrrolo[2,3-d]imidazole-5-carboxylic acid. LC-MS (ES+): m/z 306/308 (1/1) [MH+]. 1H NMR (DMSO-d6, 400 MHz): δ=7.18 (d, J=1.0 Hz, 1H), 7.86 (d, J=9.0 Hz, 2H), 7.92 (d, J=9.0 Hz, 2H), 8.69 (s, 1H), 12.15 (s, 1H, NH).

A mixture of 1-(4-bromophenyl)-1,4-dihydropyrrolo[2,3-d]imidazole-5-carboxylic acid (70 mg, 0.23 mmol), CDI (75 mg, 0.46 mmol) and DIPEA (0.1 mL) in dry THF (3 mL) was stirred at 60° C. for 1 h and then treated with 2-methoxyethylamine (0.1 mL). After additional 2 h at 60° C., the mixture was concentrated under reduced pressure, the residue suspended in water (5 mL) and the solid collected by filtration and washed with water to give 1-(4-bromophenyl)-N-(2-methoxyethyl)-1,4-dihydropyrrolo[2,3-d]imidazole-5-carboxamide EXAMPLE 3. LC-MS (ES+): m/z 363/365 (1/1) [MH+]. 1H NMR (CDCl3, 400 MHz): δ=3.41 (s, 3H), 3.57 (t, J=4.9 Hz, 2H), 3.67 (app. q, J=4.9 Hz, 2H), 6.34 (br s, 1H, CONH), 6.60 (s, 1H), 7.42 (d, J=8.7 Hz, 2H), 7.64 (d, J=8.7 Hz, 2H), 7.88 (s, 1H), 9.32 (br s, 1H, NH).

Example 4

N-(2-Methoxyethyl)-1-phenyl-1,4-dihydropyrrolo[2,3-d]imidazole-5-carboxamide

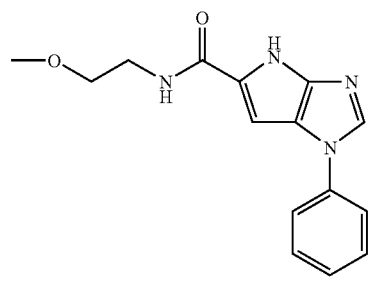

1-(4-Bromophenyl)-N-(2-methoxyethyl)-1,4-dihydropyrrolo[2,3-d]imidazole-5-carboxamide (EXAMPLE 3) was hydrogenated using the same procedure described above for EXAMPLE 2 to give N-(2-Methoxyethyl)-1-phenyl-1,4-dihydropyrrolo[2,3-d]imidazole-5-carboxamide LC-MS (ES$^+$): m/z 285 [MH$^+$].

Example 5

[1-(3-Thien-3-ylphenyl)-1,4-dihydropyrrolo[2,3-d]imidazol-5-yl]methanol

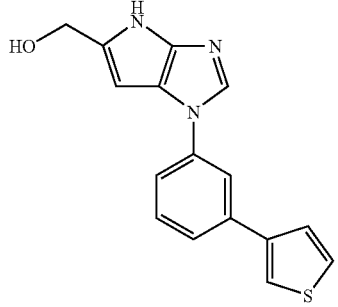

A flask containing a mixture of ethyl 1-(3-bromophenyl)-1,4-dihydropyrrolo[2,3-d]imidazole-5-carboxylate (334 mg, 1 mmol, prepared according to the procedure described for example 1 except using 3-bromoaniline in the first step) and 3-thiophene boronic acid (256 mg, 2 mmol) was degassed and placed under a nitrogen atmosphere To this was quickly added tetrakis(triphenylphosphine)palladium(0) (173.3 mg, 0.15 mmol) in one portion followed by degassed solutions of 1,4-dioxane (5 mL) and aqueous sodium carbonate (2 M, 3 mL). The reaction mixture was heated at 85° C. under nitrogen for 24 hours after which time it was cooled, filtered and concentrated in vacuo. The resulting crude material was chromatographed over silica gel eluting with MeOH:CH$_2$Cl$_2$ 0%→2%] to afford 329 mg (97.5%) of ethyl 1-(3-thien-3-ylphenyl)-1,4-dihydropyrrolo[2,3-d]imidazole-5-carboxylate. $^1$H NMR (400 MHz, CDCl$_3$): δ=8.02 (s, 1H), 7.75-7.72 (m, 1H), 7.58-7.53 (m, 3H), 7.48-7.41 (m, 3H), 6.98 (d, J=1.2 Hz, 1H), 4.37 (q, J=7.2 Hz, 2H), 1.40 (t, J=7.2 Hz, 3H). MS (ES+): m/z 338.13 (100) [MH$^+$].

To a solution of ethyl 1-(3-thien-3-ylphenyl)-1,4-dihydropyrrolo[2,3-d]imidazole-5-carboxylate (300 mg, 0.89 mmol) in dry THF (9 mL) was added lithium aluminum hydride (1.07 mL, 1.07 mmol, 1.0 M in THF) dropwise at −40° C. under nitrogen. The resulting solution was allowed to slowly warm to −20° C. over the course of 1 hour after which time the reaction was quenched with saturated aqueous ammonium chloride (3 mL) and diluted with ethyl acetate (40 mL). The suspension was filtered through Celite, the filtrate washed with saturated aqueous sodium chloride (20 mL) and then dried over anhydrous sodium sulfate and concentrated in vacuo. The crude material thus isolated was chromatographed over silica gel eluting with MeOH:CH$_2$Cl$_2$ 0%→1%→2%) to furnish 40.6 mg (15.5%) of [1-(3-thien-3-ylphenyl)-1,4-dihydropyrrolo[2,3-d]imidazol-5-yl]methanol EXAMPLE 5. $^1$H NMR (400 MHz, CDCl$_3$): δ=9.46 (s, 1H), 7.76 (s, 1H), 7.67 (t, J=2.0 Hz, 1H), 7.51-7.49 (m, 1H), 7.47-7.45 (m, 1H), 7.44-7.41 (m, 2H), 7.39-7.35 (m, 2H), 6.16 (d, J=1.2 Hz, 1H), 4.75 (s, 2H). MS (ES+): m/z 296.17 (100) [MH$^+$].

Example 6

N-Methyl-1-(3-thien-3-ylphenyl)-1,4-dihydropyrrolo[2,3-d]imidazole-5-carboxamide

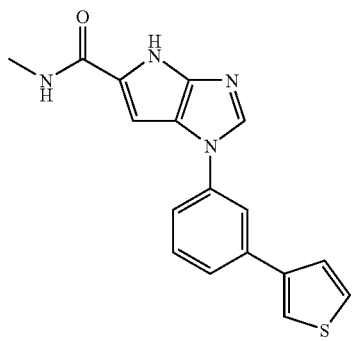

To a stirred solution of ethyl 1-(3-thien-3-ylphenyl)-1,4-dihydropyrrolo[2,3-d]imidazole-5-carboxylate (500 mg, 1.5 mmol, prepared as described in the procedure for example 5) in THF (10 mL) was added aqueous sodium hydroxide (416 mg in 4 mL H$_2$O, 10.4 mmol) and the mixture heated at reflux for 16 hr. After this time, the cooled mixture was acidified with 2M HCl to pH 6 and the resulting precipitate collected by filtration, and washed with water and hexane. The filtrate was concentrated to about half the volume and extracted with ethyl acetate (2×75 mL). The combined organic phases were washed with saturated aqueous sodium chloride, and dried over sodium sulfate and evaporated in vacuo to yield a brown solid. The solids were combined and purified by silica gel chromatography eluting with MeOH:CH$_2$Cl$_2$ 10%→25%) to yield 312.7 mg (68%) 1-(3-thien-3-ylphenyl)-1,4-dihydropyrrolo[2,3-d]imidazole-5-carboxylic acid. $^1$H NMR (400 MHz, DMSO-d$_6$): δ=8.39 (s, 1H), 8.07 (d, 2.4 Hz, 1H), 8.04-8.02 (m, 1H), 7.72-7.69 (m, 3H), 7.69-7.57 (m, 3H), 6.66 (br s, 1H). MS (ES+): m/z 338.13 (100) [MH$^+$].

A solution of 1-(3-thien-3-ylphenyl)-1,4-dihydropyrrolo[2,3-d]imidazole-5-carboxylic acid (60 mg, 0.2 mmol), EDC (44.6 mg, 0.97 mmol) and DMAP (7.1 mg, 0.06 mmol) in dry DMF (1.5 mL) was stirred at room temperature under nitrogen for 30 minutes. Methylamine (0.5 mL, 0.97 mmol, 2M solution in THF) was then added and the mixture was allowed to stir overnight at rt. After this time, water (5 mL) was added to the mixture which was extracted with DCM (3×15 mL) and the combined organic layers washed with a saturated aqueous sodium chloride (5×10 mL), then dried over anhydrous sodium sulfate and concentrated in vacuo and the resulting crude material purified by preparative TLC (5% MeOH in CH$_2$Cl$_2$) to yield 2.7 mg (4.3%) of N-methyl-1-(3-thien-3-ylphenyl)-1,4-dihydropyrrolo[2,3-d]imidazole-5-carboxamide EXAMPLE 6. $^1$H NMR (400 MHz, CDCl$_3$): δ=7.95 (br s, 1H), 7.73-7.71 (m, 1H), 7.57-7.42 (m, 6H), 6.59 (br s, 1H), 3.02 (d, J=5.2 Hz, 3H). MS (ES+): m/z 323.31 (100) [MH$^+$].

Example 7

N,N-dimethyl-1-(3-thien-3-ylphenyl)-1,4-dihydropyrrolo[2,3-d]imidazole-5-carboxamide

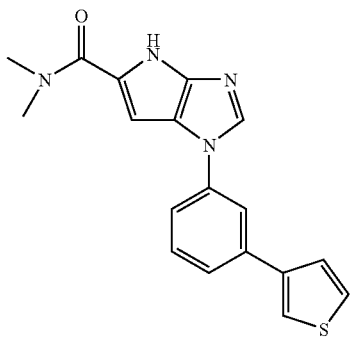

Prepared according to the procedure described for example 6 except utlising dimethylamine instead of methylamine. $^1$H NMR (400 MHz, CDCl$_3$): δ=7.94 (s, 1H), 7.74-7.71 (m, 1H), 7.59-7.53 (m, 3H), 7.48-7.42 (m, 3H), 6.60 (d, J=1.6 Hz, 1H), 3.29 (br s, 6H). MS (ES+): m/z 337.29 (100) [MH$^+$].

Example 8

N-(Pyridin-4-ylmethyl)-1-(3-thien-3-ylphenyl)-1,4-dihydropyrrolo[2,3-d]imidazole-5-carboxamide

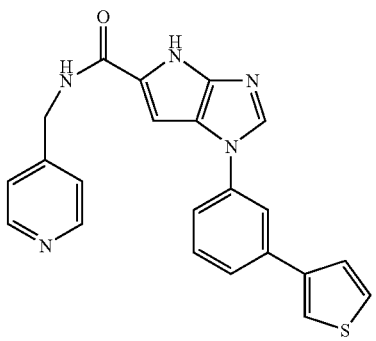

Prepared according to the procedure described for example 6 except utlising 4-aminomethylpyridine instead of methylamine. $^1$H NMR (400 MHz, CDCl$_3$): δ=7.97 (s, 1H), 7.77-7.68 (m, 2H), 7.64-7.42 (m, 7H), 6.66-6.56 (m, 2H), 2.66-2.60 (m, 2H). MS (ES+): m/z 400.29 (100) [MH$^+$].

Example 9

N-[2-(4-Morpholino)ethyl]-1-(3-thien-3-ylphenyl)-1,4-dihydropyrrolo[2,3-d]imidazole-5-carboxamide

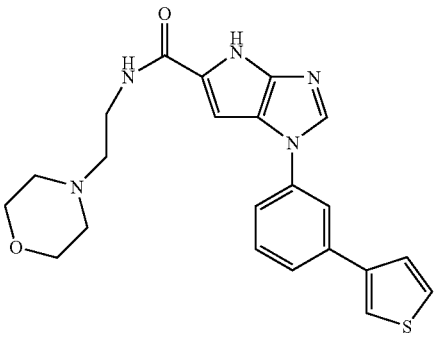

Prepared according to the procedure described for example 6 except utlising 2-morpholinoethylamine instead of methylamine. $^1$H NMR (400 MHz, CDCl$_3$): δ=8.60-8.56 (m, 2H), 7.99 (br s, 1H), 7.73-7.71 (m, 1H), 7.57-7.54 (m, 3H), 7.47-7.41 (m, 3H), 7.30-7.27 (m, 3H), 6.68 (br s, 1H), 6.37-6.30 (m, 1H), 4.68 (d, J=6.4 Hz, 2H), 3.49 (s, 4H). MS (ES+): m/z 422.30 (100) [MH$^+$].

Example 10

Methyl 1-(3-thien-3-ylphenyl)-1,4-dihydropyrrolo[2,3-d]imidazole-5-carboxylate

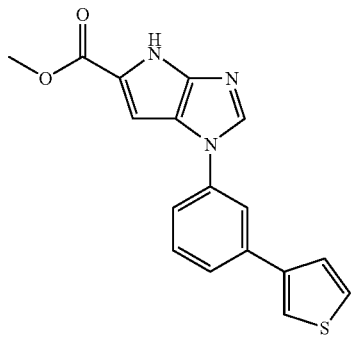

To a stirred solution of 1-(3-thien-3-ylphenyl)-1,4-dihydropyrrolo[2,3-d]imidazole-5-carboxylic acid (200 mg, 0.65 mmol, prepared as described in the procedure for example 6) in methanol (10 mL) was added concentrated sulfuric acid (5 drops). The solution was heated at reflux for 36 h then cooled to room temperature, basified with aqueous sodium bicarbonate (40 mL) and extracted with CH$_2$Cl$_2$ (2×40 mL). The combined organic extracts were washed with saturated aqueous sodium chloride, dried over sodium sulfate and concentrated in vacuo. The resulting residue was purified twice by silica gel chromatography eluting with MeOH:CH$_2$Cl$_2$ 0%→1%) to yield 63.4 mg (30.3%) of methyl 1-(3-thien-3-ylphenyl)-1,4-dihydropyrrolo[2,3-d]imidazole-5-carboxylate EXAMPLE 10. $^1$H NMR (400 MHz, CDCl$_3$): δ=10.11 (br s, 1H), 8.08 (s, 1H), 7.76-7.74 (m, 1H), 7.58-7.51 (m, 3H), 7.47-7.42 (m, 3H), 6.99 (d, J=1.6 Hz, 1H), 3.93 (s, 3H). MS (ES+): m/z 324.23 (100) [MH$^+$].

Definitions: EDC=ethyl dimethylaminopropylcarbodiimide hydrochloride, HOAt=1-hydroxyazabenzotriazole, HOBt=1-hydroxybenzotriazole, CDI=1,1'-carbonyldiimidazole, TBTU=O-benzotriazole-N,N,N',N'-tetramethyl uronium tetrafluoroborate, HATU=azabenzotriazolyl-N,N,N',N',-tetramethyluronium hexafluorophosphate, DIPEA=diisopropylethylamine, TEA=triethylamine, DMF=N,N-dimethylformamide, NMP=N-methylpyrrolidinone, DCM=dichloromethane, DMAP=4-dimethylaminopyridine, TFA=trifluoroacetic acid, Boc=tbutoxycarbonyl, Fmoc=fluorenylmethyloxycarbonyl, DMSO=dimethylsulphoxide, AcOH=acetic acid, OMs=$OSO_2Me$, OTs=$OSO_2$-(4-Me)Ph, OTf=$OSO_2CF_3$, DPPF=, $Pd_2(dba)_3$, NBS=N-bromosuccimimide, HCl (aq)=aqueous hydrochloric acid, DMA=N,N-dimethylacetamide, MeOH=methanol, EtOH=ethanol, HOAc=acetic acid, EtOAc=ethyl acetate, THF=tetrahydrofuran, hplc=high performance liquid chromatography, PS-TFP=polystyrene-supported tetrafluorophenol resin, PS-HOBt=polystyrene-supported 1-hydroxybenzotriazole resin, DIC=1,3-diisopropylcarbodiimide, IMS=industrial methylated spirit, NMM=N-methyl morpholine, Pd/C=palladium on carbon, $Pd(PPh_3)_4$=tetrakis(triphenylphosphine)palladium (0), $Cs_2CO_3$=cesium carbonate, $Pd_2(dba)_3$=tris(dibenzylideneacetone)dipalladium (0), BINAP=1,1'-binaphthyl, $Pd(OAc)_2$=palladium (II) acetate, $K_2CO_3$=potassium carbonate, MeCN=acetonitrile, DCC=1,3-dicyclohexylcarbodiimide, HPLC=high performance liquid chromatography, rt or r.t.=room temperature, MTP=microtitre plate, min=minute(s), h=hour(s), d=day(s).

The EXAMPLES of this invention reduced the level of SCF-induced tyrosine phosphorylation of Kit in intact H526 cells as determined in the above assay with IC50 values between 4 μM and 0.027 μM.

What is claimed is:

1. A compound represented by Formula (I)

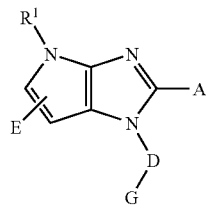

(I)

or a pharmaceutically acceptable salt or N-oxide thereof, wherein

A is $C_{0-6}$alkyl or $-NR^1R^{11}$;

E is $-CO_2R^2$, $-CONR^{12}R^{21}$, $-C(R^aR^b)OR^{212}$, or $-C(R^aR^b)NR^{12}R^2$;

D is aryl or hetaryl;

G is $C_{0-6}$alkyl, halogen, optionally substituted cyclyl, optionally substituted heterocyclyl, $-OR^{22}$, $-NR^{13}R^{22}$, $-CN$ or $-CF_3$;

$R^1$, $R^{11}$, $R^{12}$, $R^{212}$, and $R^{13}$ each independently is $C_{0-6}$alkyl, $-COR^{14}$, $-CONR^{14}R^{15}$, or $-S(O)_nNR^{14}R^{15}$;

$R^{14}$ and $R^{15}$ each independently is $C_{0-6}$alkyl, $-CO(C_{0-6}$alkyl), $-CON(C_{0-6}$alkyl)($C_{0-6}$alkyl), or $-S(O)_mN(C_{0-6}$alkyl)($C_{0-6}$alkyl);

$R^2$ and $R^{22}$ each independently is $C_{1-8}$alkyl optionally substituted with a heterocyclyl; $-C_{0-8}$alkyl-$C_{3-8}$cycloalkyl, $-C_{2-8}$alkyl-O—$C_{0-8}$alkyl, $-C_{2-8}$alkyl-N($C_{0-8}$alkyl)($C_{0-8}$alkyl), $-C_{2-8}$alkyl-S(O)$_{0-2}$—$C_{0-8}$alkyl; or heterocyclyl optionally substituted with $C_{0-8}$alkyl, cyclyl or substituted cyclyl substituent;

$R^{21}$ is $C_{0-8}$alkyl optionally substituted with a heterocyclyl; $R^{21}$ is $-C_{0-8}$alkyl-$C_{3-8}$cycloalkyl, $-C_{2-8}$alkyl-O—$C_{0-8}$alkyl, $-C_{2-8}$alkyl-N($C_{0-8}$alkyl)($C_{0-8}$alkyl), or $-C_{2-8}$alkyl-S(O)$_{0-2}$—$C_{0-8}$alkyl; or $R^{21}$ is heterocyclyl optionally substituted with $C_{0-8}$alkyl, cyclyl or substituted cyclyl substituent;

$R^a$ and $R^b$ are each independently $C_{0-8}$alkyl or $C_{3-8}$cycloalkyl;

or $R^a$ and $R^b$ taken together with the C to which they are attached form a saturated or partially unsaturated 3-10 membered ring optionally containing 0-4 N, O, S, SO, or $SO_2$ at the ring nodes, provided that no N, O or S atoms are placed adjacent to each other at ring nodes; and n and m each independently is 0, 1, or 2.

2. The compound according to claim 1, wherein A is $C_{0-6}$alkyl; or a pharmaceutically acceptable salt or N-oxide thereof.

3. The compound according to claim 2, wherein E is $-CO_2R^2$; or a pharmaceutically acceptable salt or N-oxide thereof.

4. The compound according to claim 2, wherein E is $-CONR^{12}R^{21}$; or a pharmaceutically acceptable salt or N-oxide thereof.

5. The compound according to claim 2, wherein E is $-C(R^aR^b)OR^{212}$; or a pharmaceutically acceptable salt or N-oxide thereof.

6. The compound according to claim 2, wherein E is $-C(R^aR^b)NR^{12}R^2$; or a pharmaceutically acceptable salt or N-oxide thereof 7. The compound according to claim 1, wherein A is $-NR^1R^{11}$; or a pharmaceutically acceptable salt or N-oxide thereof.

8. The compound according to claim 1, wherein D is aryl, or a pharmaceutically acceptable salt or N-oxide thereof.

9. The compound according to claim 8, wherein G is $C_{0-6}$alkyl, or a pharmaceutically acceptable salt or N-oxide thereof.

10. The compound according to claim 8, wherein G is halogen, or a pharmaceutically acceptable salt or N-oxide thereof.

11. The compound according to claim 8, wherein G is optionally substituted heterocyclyl, or a pharmaceutically acceptable salt or N-oxide thereof.

12. A composition comprising a compound according to claim 1, or a pharmaceutically acceptable salt or N-oxide thereof, and a pharmaceutically acceptable carrier.

13. A compound according to claim 1 consisting of

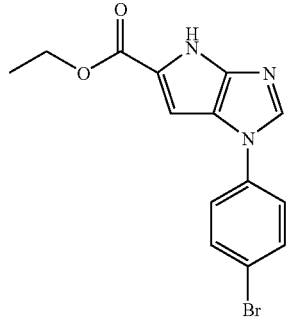

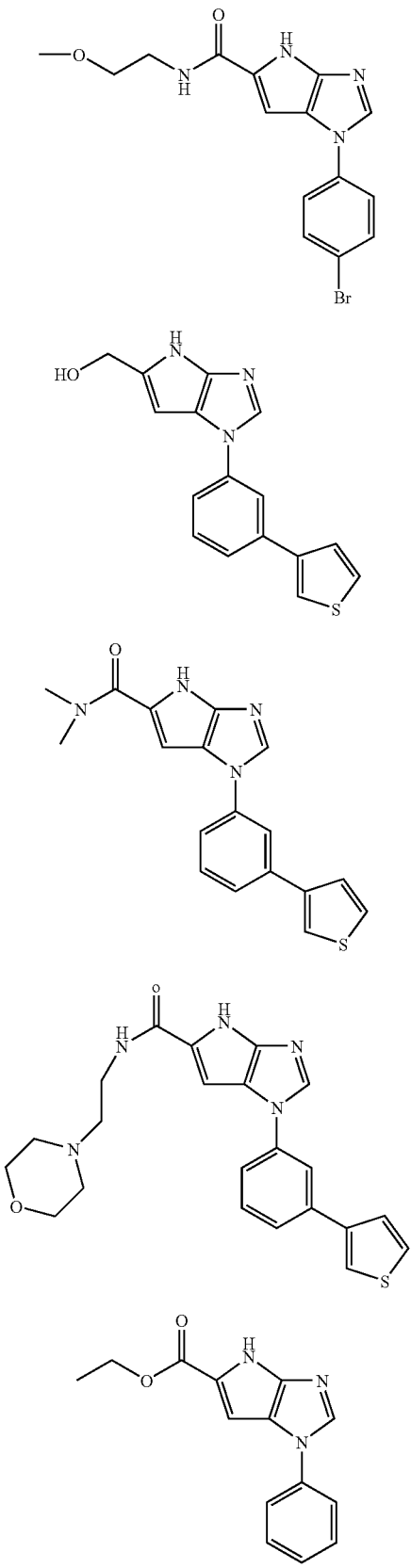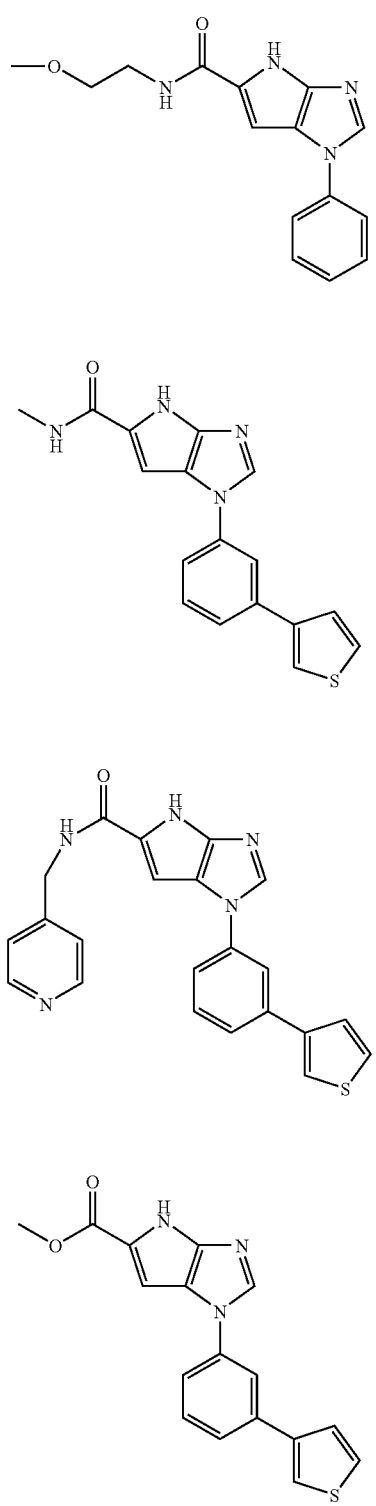
or a pharmaceutically acceptable salt or N-oxide thereof.
* * * * *